United States Patent
Asano et al.

(10) Patent No.: US 6,358,884 B1
(45) Date of Patent: Mar. 19, 2002

(54) BACTERIOCIDAL AND FUNGICIDAL SOLUTION CONTAINING INORGANIC SILVER COMPLEX SALT AND PROCESS FOR PRODUCING THE SAME

(75) Inventors: Satoshi Asano, Niihama; Shinji Esaki, Tokyo; Hideaki Nishihara, Niihama, all of (JP)

(73) Assignee: Sumitomo Metal Mining Co., Ltd., Tokyo (JP)

( * ) Notice: Subject to any disclaimer, the term of this patent is extended or adjusted under 35 U.S.C. 154(b) by 0 days.

(21) Appl. No.: 09/486,122

(22) PCT Filed: May 6, 1998

(86) PCT No.: PCT/JP98/02010

§ 371 Date: Mar. 21, 2000

§ 102(e) Date: Mar. 21, 2000

(87) PCT Pub. No.: WO99/09833

PCT Pub. Date: Mar. 4, 1999

(30) Foreign Application Priority Data

Aug. 25, 1997 (JP) .............................. 9-227673

(51) Int. Cl.⁷ ............................................... A01N 59/16
(52) U.S. Cl. ........................ 504/187; 504/152; 504/144; 424/618; 426/335
(58) Field of Search ................................. 424/618, 619, 424/DIG. 6; 504/187, 152, 114; 426/335

(56) References Cited

U.S. PATENT DOCUMENTS 4,043,932 A * 8/1977 Fresenius et al. .............. 252/95
5,662,913 A * 9/1997 Capelli ........................ 424/405

FOREIGN PATENT DOCUMENTS

| JP | 5116234 | 2/1976 |
| JP | 6271412 | 9/1994 |
| JP | 8225418 | 9/1996 |

* cited by examiner

Primary Examiner—John Pak
(74) Attorney, Agent, or Firm—Dykema Gossett PLLC

(57) ABSTRACT

A bactericidal and fungicidal solution is made by a method wherein an aqueous solution containing ammonium chloride or a chloride of an alkali metal or alkaline earth metal as chloride ions is prepared, a silver salt or metallic silver is added to the aqueous solution and silver ions are dissolved as a chloro complex salt. The aqueous solution exhibits a bactericidal effect at a concentration of silver ions contained as the chloro complex salt of 0.05 mg/liter or more and a bactericidal and fungicidal effect at a concentration of 0.5 mg/liter or more.

3 Claims, 3 Drawing Sheets

BACTERIOCIDAL AND FUNGICIDAL SOLUTION CONTAINING INORGANIC SILVER COMPLEX SALT AND PROCESS FOR PRODUCING THE SAME

This application is a 371 of PCT/JP98/02010, filed on May 6, 1998.

BACKGROUND OF THE INVENTION

1. Field of the Invention

This invention concerns a bacteriocidal and fungicidal solution containing an inorganic silver complex which is effective for bacteriocidal and fungicidal use with all articles such as daily necessaries and industrial products, as well as a production process therefor.

2. The Prior Art

Recently, various products containing bacteriocidal and fungicidal agents, including sanitary porcelains as well as daily necessaries such as stationaries, have been provided. Such products are imparted with bacteriocidal and fungicidal ability by kneading water soluble organic bacteriocides or less soluble compounds of metals such as silver having a bacteriocidal effect into the materials used to make the products, or by fixing them on the surfaces of the products.

However, even such products having bacteriocidal and fungicidal agents previously used for bacteriocidal and fungicidal treatment involve a drawback of reduced bacteriocidal and fungicidal activity when the surfaces of the products are covered with stains or when silver is sulfurized when silver compounds are used as the bacteriocidal and fungicidal agents.

Further, since bacteriocidal and fungicidal agents used for the bacteriocidal and the fungicidal agent-incorporated products are in the form of powdery or like other solid form, they have to be fixed previously on the surfaces of the products by kneading or special treatment.

Therefore, the solid state bacteriocidal and fungicidal agents have a disadvantage that they can not be used by a method such as spraying on the surfaces of usual articles which are being used, for example, in homes in a case where it is intended to subsequently impart the bacteriocidal and fungicidal ability to the articles.

While on the other hand, liquid or water soluble bacteriocidal and fungicidal agents are also used although the application use is restricted. Among them, bacteriocidal and fungicidal agents of alcohols, phenols such as cresol, quaternary ammonium salts or silver complex salts comprising metals having sterilizing effect such as silver and amino acid, thiosulfate or thiocyanate have been put to practical use, and addition of bacteriocidal and fungicidal agents comprising silver thiosulfate to water in a vase has been adopted, for example, for keeping cut flowers long.

The existent liquid or water soluble bacteriocidal and fungicidal agents have an advantage capable of subsequently imparting the bacteriocidal and fungicidal ability by merely applying them on the surfaces of usual articles which are being used. However, as a problem in common with such bacteriocidal and fungicidal agents, there has been a significant drawback that they are leached out almost substantially upon water washing even when applied to the surfaces of articles, to easily lose the effect.

Moreover, the alcoholic or phenolic bacteriocidal and fungicidal agents are effective only temporarily because of their volatility and easy oxidizability and, particularly, there is a problem in view of safety that the alcoholic agents are highly flashing and phenolic agents give toxicity and keen stimulative odors. Further, the quaternary ammonium salt type bacteriocidal and fungicidal agents involve a drawback that they react with daily used anionic surfactants such as soaps or detergents, to easily loss sterilizing ability.

Furthermore, in a case of the bacteriocidal and fungicidal agents of silver complex salt type, since complex salts of silver with thiosulfate or thiocyanate contain $S^{2-}$ ions, they are decomposed by acid or heat to evolve noxious gases and the effective ingredients are gradually converted to silver sulfide to loss the sterilizing ability. Further, the organic complex salts such as amino acid salts of silver have relatively low complex stability compared with other inorganic complex salts containing $S^{2-}$ ions and, accordingly, they react with chloride ions which are usually present in ordinary circumstances tending to precipitate silver chloride and, as a result, the bacteriocidal and fungicidal effect is remarkably lowered. Further, like that the inorganic silver salts to be described later, they are sometimes blackened when deposited to skins and, in addition, they are difficult to be synthesized industrially compared with inorganic salts to require more production cost.

On the other hand, as traditional water soluble bacteriocidal and fungicidal agents, water soluble inorganic silver salts such as silver nitrate have been known. However, the silver nitrate and the like, although water soluble, have a serious problem that they cause precipitation of silver chloride in the inside of skins upon deposition on the skins which are reduced and blackened, as well as they are decomposed to be blackened while releasing silver by ultraviolet rays and difficult to be stored., so that they are scarcely used at present as bacteriocidal agents and fungicidal agents.

SUMMARY OF THE INVENTION

In view of the foregoing situations in the prior art, it is an object of this invention is to provide an bacteriocidal and fungicidal solution in liquid form which can impart bacteriocidal and fungicidal ability by subsequent application to the surfaces of usual products used in homes and the like, is not volatile and odorless or not deactivated for the effect by heat, acids, ultraviolet rays or anionic surfactants and retains its effect even by water washing, as well as a production process therefor.

The bacteriocidal and fungicidal solution according to this invention for attaining the foregoing purpose has a feature of containing silver ions of 0.05 mg/liter or more as a chloro complex salt in an aqueous solution containing ammonium chloride or a chloride of an alkali metal or alkaline earth metal as chloride ions.

Further, a process for producing a bacteriocidal and fungicidal solution according to this invention has a feature of preparing an aqueous solution containing ammonium chloride, or a chloride of an alkali metal or alkaline earth metal as chloride ions, adding a silver salt or metallic silver to the aqueous solution and dissolving silver ions of 0.05 mg/liter or more as a chloro complex salt.

Further, the bacteriocidal and fungicidal solution is effective both for bacteriocidal and fungicidal uses when the concentration of the silver ions contained as the chloro complex salt is 0.5 mg/liter or more but the effect is restricted to the bacteriocidal effect, since it is poor in the fungicidal effect although effective for the bacteriocidal effect at a concentration lower than the above.

DETAILED DESCRIPTION OF THE PREFERRED EMBODIMENTS

Figure 1:
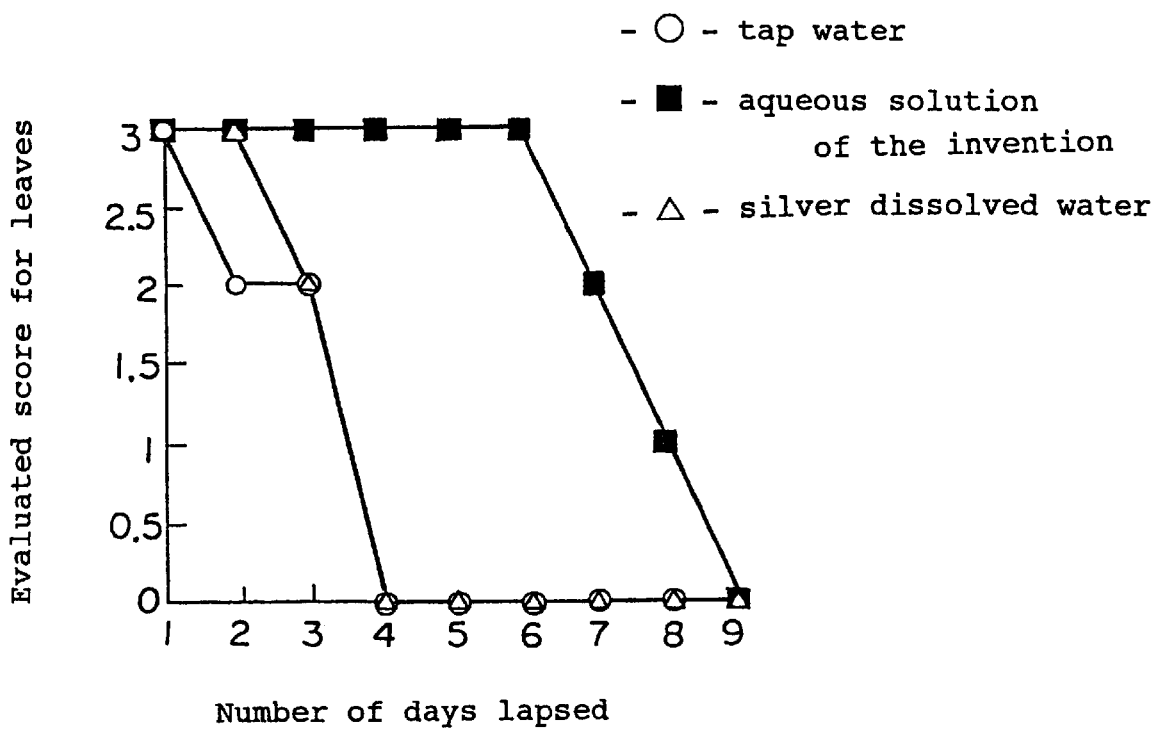
FIG. 1 is a graph showing a relationship between the number of days lapsed and the evaluation score for the state of leaves in a test for keeping cut flowers long.

According to the bacteriocidal and fungicidal solution of this invention, silver ions known to have a bacteriocidal and fungicidal effect against wide variety of bacteria and fungi are stabilized by being dissolved into an aqueous solution of ammonium chloride or a chloride of an alkali metal or alkaline earth metal to form a chloro complex chloro salt of silver. The bacteriocidal and fungicidal solution can simply impart the bacteriocidal and fungicidal ability subsequently by applying them on the surfaces of usual products used in home and the like by spraying or like other means.

As shown by the following chemical formula (1), silver ions in the aqueous solution react with chloride ions to form precipitation of silver chloride. Silver chloride is less water soluble and solubility to water is only at 1.3 mg/liter at 15° C.

$$Ag^+ + Cl^- \rightarrow AgCl \qquad (1)$$

However, as the concentration of chloride ions in the aqueous solution is increased, the solubility of silver chloride is once lowered due to common ion effect of anions as far as $3 \times 10^{-3}$ mol/liter but, since water soluble dichloroargentate ions are formed by the reaction of the following chemical formula (2) when the concentration of the chloride ions is exceeded, the solubility of silver chloride increases gradually. Then, when the concentration of the chloride ions exceeds $5 \times 10^{-2}$ mol/liter, silver chloride exhibits higher solubility than the solubility to water and, finally, it is possible to obtain an aqueous solution containing silver ions at the order of several g/liter at the maximum as a chloro complex salt.

$$AgCl + Cl^- \rightarrow AgCl_2^- \qquad (2)$$

On the other hand, according to "Metal", vol. 65 (1995), No. 11, p1061–1064 published from Agne Co., it has been known that silver ions show a slow releasing bacteriocidal effect at 0.05 mg/liter or more and shows a slow releasing fungicidal effect at 0.5 mg/liter or more.

Accordingly, referring to the concentration of the silver ions in the bacteriocidal and fungicidal solution, the bacteriocidal effect can be expected if it is 0.05 mg/liter or more. Considering, however, that it is often used by being sprayed on moistened fiber cloth and the like in a case for home use, it is preferred that the concentration is at 0.5 mg/liter or more and, further preferably, 5 mg/liter or more in a state of a stock solution so as to give the above-mentioned concentration in a diluted state.

Further, both of the bacteriocidal and fungicidal effects can be expected when the concentration of the silver ions is 0.5 mg/liter or more. However, by the same reason as described above, it is preferred that the concentration is 5 mg/liter or more and, more preferably, 50 mg/liter or more in the state of the stock solution. However, when the concentration of the silver ions exceeds 8 g/liter, silver can not be dissolved stably in the liquid but tends to form precipitates even if the concentration of the chloride is high in the aqueous solution, so that the concentration of the silver ions is preferably about 5 g/liter at the highest in view of the stability as the product.

On the other hand, the concentration of the chloride ions in the aqueous solution can be determined properly depending on the required concentration of the silver ions. For instance, the silver ions can be dissolved as complex chloro salt if the concentration of the chloride ions is $3 \times 10^{-3}$ mol/liter, but it is necessary to adjust the concentration of the chloride ions to $5 \times 10^{-2}$ mol/liter or more in order to increase the concentration of the silver ions to higher than that for the solubility to water. The upper limit for the concentration of the chloride ions is a concentration required for dissolving the silver ions at the highest concentration of 5 g/liter, for which about 10 mol/liter is enough.

The chloro complex salt of silver of this invention differs most significantly from existent silver complex salts and silver compounds in the stability to heat, acids, ultraviolet rays and chlorides. That is, since the chloro complex ions of silver contain no $S^{2-}$ as in the thiocyanate complex ions or thiosulfate complex ions used generally so far, they do not form sulfides by heat or acids. Further, while a standard electrode potential $E^0$ between $AgCl + e^- = AgCl^-$ is 0.22 V, it is substantially 0 V between $AgCl_2^- + e^- = Ag + 2Cl^-$ when the concentration of the chloride ions is 1 mol/liter and the potential is further lowered as the concentration of the chloride ions increases, so that the chloro complex salt of silver ions are stable also to ultraviolet rays or reduction.

Accordingly, the bacteriocidal and fungicidal solution comprising the chloro complex salt of silver according to this invention can be stored for a long period of time being filled in a transparent container and is not blackened even when it is in contact with skins.

Further, even when it is in contact with chloride ions, since the chloride ions have already been in the form of ligands, silver chloride is not precipitated while the solubility may rather increase due to excess chloride ions.

Further, the bacteriocidal and fungicidal solution according to this invention can simply impart the bacteriocidal and fungicidal ability to usual products used in homes and the like by applying on the surface of the articles, for example, by spraying and like other means. Further, the bacteriocidal ability of the articles deposited with the chloro complex salt or complex ions of silver is not lowered easily even by water washing. This feature is a characteristic not found in other water soluble bacteriocidal and fungicidal agents. This is because the reaction reverse to the chemical formula (2) is taken place by water washing and the fine particles of silver chloride are formed and adsorbed on the surface of the articles. Adsorption of the fine particles of silver chloride occurs only on the surface of the articles and, since they do not deposit on skins and the like upon water washing, no subsequent blackening occurs by ultraviolet rays to skins or the like.

The bacteriocidal and fungicidal solution according to this invention can be produced by adding ammonium chloride or a chloride of an alkali metal or alkaline earth metal to water so as to provide a predetermined concentration thereby preparing an aqueous solution, adding a silver salt industrially available at a reduced cost such as silver nitrate, sulfate or chloride (which is water insoluble) or silver metal to the aqueous solution and dissolving silver as dichloroargentate complex ions as shown by the chemical formula (1) above. Accordingly, since this can be produced with no requirement of using expensive starting materials such as organic silver salts or utilizing complicate double decomposition, it can be produced at a reduced cost and simply.

The chloride used includes, generally, chlorides of alkali metals such as sodium or potassium and alkaline earth metals such as magnesium or calcium in addition to ammonium chloride. Further, since chlorides of alkaline earth metals have higher permeability than the ammonium chloride or chlorides of alkali metals, they are preferred in general application uses. However, in a case of the chlorides of the alkaline earth metals, since they may sometimes form precipitates when mixed with the anionic surfactants, ammonium chloride or the chloride of alkali metal is suitable to such an application use. However, since silver ions are not precipitated in any of the cases, the bacteriocidal and fungicidal effects are not lost.

While there are various chlorides which are usable in view of principle other than ammonium chloride and chlorides of alkali metals or alkaline earth metals, they are not preferred since they lack in general utilizability due to the reason that ions themselves are colored, or they shows acidic nature upon hydrolysis and are toxic and not economical because of high cost.

Further, since the bacteriocidal or fungicidal effect can be attained generally when the silver ion concentration is 0.05 mg/liter or more, it may be considered that silver may be used as the bacteriocidal and fungicidal agent not contained in the state of the chloro complex salt but in the form of an aqueous solution of silver chloride. How ever, since silver chloride is easily decomposed by ultraviolet rays even in a state of the aqueous solution to form metallic silver soluble only to about 0.03 mg/liter to water, it is extremely difficult to be stored and is not practical.

EXAMPLE

Example 1
[Fungicidal Test Using Bread]

As a bacteriocidal and fungicidal solution according to this invention, silver chloride was dissolved into an aqueous solution of calcium chloride at 3 mol/liter to obtain an aqueous solution containing 0.5 g/liter of silver as a chloro complex salt. For evaluation of the fungicidal effect of the aqueous solution, 2 g of the aqueous solution was uniformly sprayed on the surface of 15 g (50 mm×50 mm) of bread and left in a room at a humidity of 90% and at a temperature of 25° C. in an open state for 20 days, together with 15 g (50 mm×50 mm) of bread without application of spraying as a comparative example.

As a result, fungi appeared to the bread with no spraying (comparative example) after lapse of five days and the entire surface was covered with fungi after lapse of 20 days, whereas occurrence of fungi was not recognized at all even after lapse of 20 days for the bread sprayed with the aqueous solution (Example 1). Further it was confirmed that the aqueous solution showed the fungicidal effect even after left in the open state for a long period of time, different from the alcoholic bacteriocidal and fungicidal agent.

Example 2
[Bacteriocidal Test for Staphylococcus aureus]

Using the same aqueous solution containing silver as the chloro complex salt as in Example 1 above a bacteriocidal effect to Staphylococcus aureus was evaluated. As a comparison, a bacteriocidal test was conducted in the same manner by using a sterilizing ethanol as a bacteriocidal agent instead of the aqueous solution described above. The evaluation method is as shown below.

Each of the test specimen solutions was sprayed each about by 1 g as the bacteriocidal agent do so as to be substantially uniform by using a spray on 5A filter paper of 11 cm diameter and then each filter paper was left in a room with no air conditioning facility at a room temperature for 24 hours. Subsequently, a bacteria solution adjusted to a cell number of $7 \times 10^4$ N/ml by a preliminary test was dropped each by 1 ml by using a micro-pipette to each filter paper and further left in a room with no air conditioning facility at a room temperature for 24 hours.

Then, each filter paper was transferred to a sterilized cup, and vigorously shaken for 2 min by a shaker with addition of 100 ml of water. Subsequently, 1 ml of a test solution was sampled from each of sterilized cups, subjected to plate culture at 36° C. for 72 hours each with addition of ordinary agar culture medium, and the number of colonies formed was counted.

Further as a blank test, 1 ml of a solution diluted by 100 times from the bacterial solution described above (the number of cells about $7 \times 10^4$ N/ml) was sampled to a Shale without using the bacteriocidal agent, cultivated in the same manner as described above with addition of a usual agar medium, and the number of formed colonies was counted.

As a result obtained from each of the tests, number of cells in the Shale, number of cells per filter paper (1 ml of bacterial solution) and the increase/decrease ratio (%) to the number of cells dropped to filter paper ($7 \times 10^4$ N/ml) are shown in the following Table 1.

TABLE 1

| Specimen solution of bacteriocidal agent | Number of cells in Shale | Number of cells per filter paper | Increase/ decrease ratio for Number of cell |
| --- | --- | --- | --- |
| Aqueous solution of the invention | 52 | $5.2 \times 10^3$ | 7.4% |
| Sterilizing ethanol | 507 | $5.1 \times 10^4$ | 72.9% |
| None (blank test) | 731 | $7.3 \times 10^4$ | 104% |

As can be seen from the result of the Table 1, it was recognized that the aqueous solution containing the chloro complex salt of silver according to this invention had an extremely strong bacteriocidal effect compared with the sterilizing ethanol and the blank test.

While the cultivation time was 72 hours in the evaluation test described above, when they were compared at the cultivation time of 48 hours, colonies were already formed in the Shale for the sterilizing ethanol and the blank test, whereas no colonies were recognized in the Shale for the aqueous solution according to this invention. Accordingly, it is considered that while bacteria in the Shale did not die but the activity of the bacteria was weakened with the aqueous solution according to this invention.

Example 3
[Bacteriocidal and Fungicidal Test by Moistened Cloth]

After suspending one gram of a flaky powder of metallic silver into an aqueous solution of calcium chloride at 3 mol/liter for one hour, it was filtered to obtain an aqueous solution. Silver was dissolved as a chloro complex salt by 1.5 mg/liter in the resultant aqueous solution.

Two sheets of cotton fabrics impregnated with 25 ml of bath water after being used for bathing were provided, and 1 ml of an aqueous solution containing the chloro complex salt of silver described above was sprayed to one of them and the other of them was used as it was (not sprayed), and both of cotton fabrics were stored in a tightly closed state at 25 ° C. for 10 days. The concentration of silver ions contained in the cotton fabrics sprayed with the aqueous solution was 0.057 mg/liter.

When odors of each of cotton fabrics were confirmed after lapse of 10 days, keen rancid odor was felt for the not sprayed cotton fabric, whereas such rancid odor was not felt for the cotton fabric sprayed with the aqueous solution described above. However, occurrence of fungi was recognized also for the sprayed cotton fabric. From the result, it was found that the aqueous solution at the concentration of silver ions of 0.057 mg/liter shows the bacteriocidal effect against bacteria concerned with formation of malodors, although it had little fungicidal effect.

Example 4
[Test for Keeping Cut Flowers Long]

Two red roses were paired to one set as a test specimen and the following comparative tests ①→③ were conducted.

That is;

Test ① (tap water): Cut roses were inserted as they were in a vase filled with tap water and water, was not replaced.

Test ② (aqueous solution of this invention): After depositing the same aqueous solution as in Example 1 to cut ends of rose stalks they were inserted into a vase filled with tap water, and water was not replaced.

Test ③ (silver dissolved water): Silver plate was immersed in tap water to dissolve silver to a saturated state at about 0.04 mg/liter, and cut roses were inserted in a vase filled with water containing silver dissolved therein, and water was not replaced.

The amount of water filled in the vases was 200 ml and the ambient temperature was 28° C. uniformly in each of the tests described above. The states of leaves, flowers and stalks were observed on every lapse of a predetermined number of days and evaluation scores were determined by the evaluation method shown in the following Table 2, and the relationship between the number of days lapsed and the evaluation score was examined on every observed portions to quantize the qualitative observation. In this evaluation method, longer life keeping effect was recognized as the evaluation score was higher. The results of evaluation are shown in FIG. 1 to FIG. 3.

TABLE 2

| Stalks | no change | score 2 |
| | with some slime | score 1 |
| | with complete slime | score 0 |
| Flower | no change | score 5 |
| | drooped for one-half | score 4 |
| | discolored for one half | score 3 |
| | entirely discolored | score 2 |
| | entirely drooped | score 1 |
| | dead | score 0 |
| Leaves | no change | score 3 |
| | drooped for one-half | score 2 |
| | drooped entirely | score 1 |
| | dead | score 0 |

Figure 2:
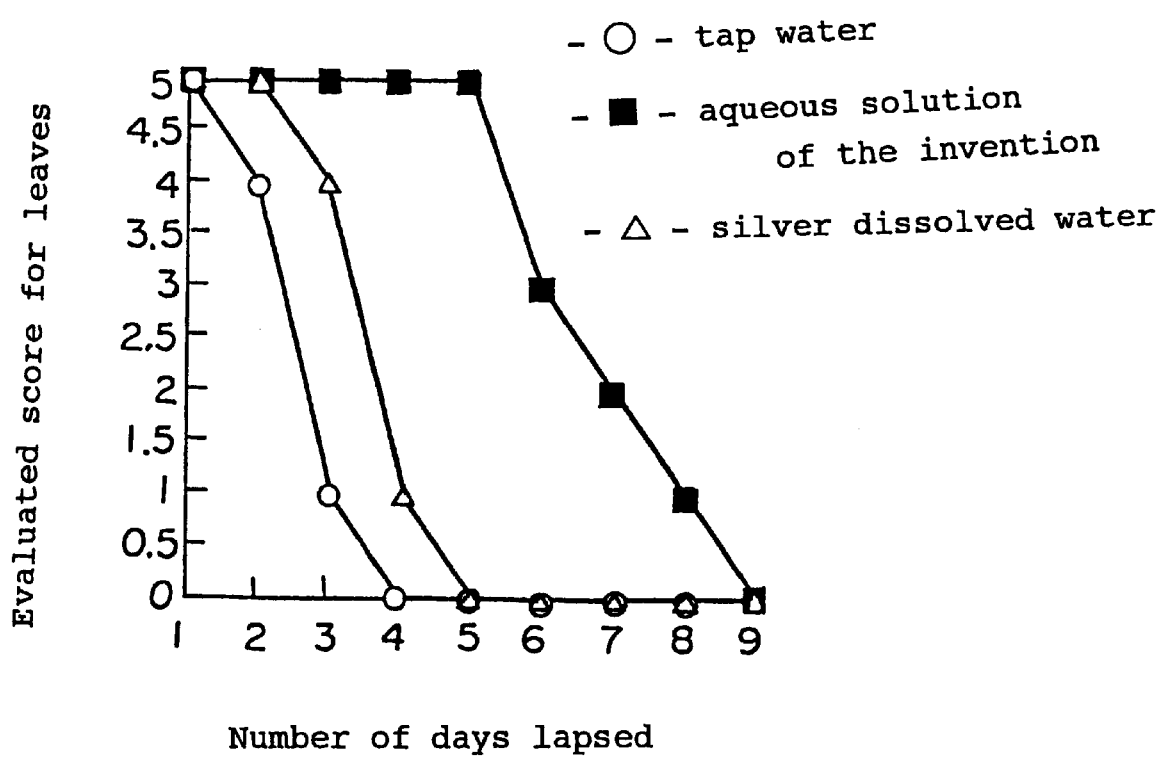
FIG. 2 is a graph showing a relationship between the number of days lapsed and the evaluation score for the state of flowers in a test for keeping cut flowers long.
Figure 3:
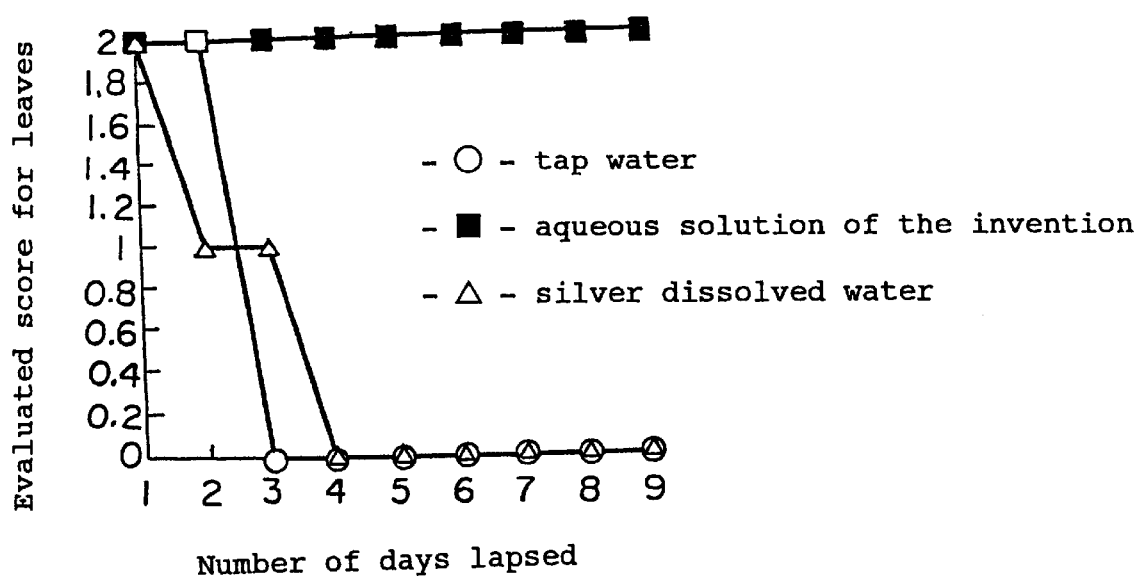
FIG. 3 is a graph showing a relationship between the number of days lapsed and the evaluation for the slimy state of stalks in a test for keeping cut flowers long.

As can be seen from the results of FIG. 1 to FIG. 3, in cut roses to which the aqueous solution containing the silver chloro complex salt according to this invention (■) was deposited to the cut ends of stalks since the bacteriocidal effect of the chloro complex salt of silver was provided even when they were immersed in water, and proliferation of bacteria at the cut faces of the stalks was inhibited and, as a result, a remarkable effect was recognized to both of keeping of flowers and leaves longer and prevention of slime on the stalks.

On the contrary, it was found that cut ends of stalks were rotten and clogged by proliferation of bacteria making it difficult or impossible for preservation, so that the life of flowers and leaves were shortened merely by tap water (○) or water to which silver was dissolved to its saturation (Δ).

(Industrial Applicability)

As has been described above according to this invention, it is possible to provide a bacteriocidal and fungicidal solution which can be produced at a reduced cost, is not volatile and odorless, can be stored for a long period of time and can impart bacteriocidal and/or fungicidal ability by subsequent application by a method such as coating to the surfaces of usual articles used in homes and the like. In addition, the bacteriocidal and fungicidal solution has extremely strong bacteriocidal and fungicidal effect, does not lose its effect by heat, acids or anionic surfactants and the like, and can maintain the long lasting effect even after water washing or in water.

What is claimed is:

1. A process for producing an aqueous bactericidal and fungicidal solution which consists of the steps of: (a) preparing an aqueous solution containing only ammonium chloride or a chloride of an alkali metal or an alkaline earth metal, and (b) adding a water-insoluble silver salt or metallic silver to the aqueous solution of (a) to obtain the aqueous bactericidal and fungicidal solution containing at least 0.05 mg/liter of silver as a dissolved chloro complex salt.

2. A process for producing a bactericidal and fungicidal solution as defined in claim 1, wherein the aqueous solution of step (a) contains at least $5 \times 10^{-2}$ mol/liter of chloride ions.

3. A process according to claim 1, wherein said water-insoluble silver salt is silver chloride.

\* \* \* \* \*